(12) United States Patent
Serban et al.

(10) Patent No.: US 9,074,983 B2
(45) Date of Patent: Jul. 7, 2015

(54) DEPOSITION OF SENSING LAYERS FOR SURFACE ACOUSTIC WAVE CHEMICAL SENSORS BASED ON SUPRA-MOLECULAR CHEMISTRY

(75) Inventors: Bogdan Catalin Serban, Bucharest (RO); Viorel V. Avramescu, Bucharest (RO); Cornel P. Cobianu, Bucharest (RO); Ion Georgescu, Bucharest (RO); Nicolae Varachiu, Bucharest (RO)

(73) Assignee: Honeywell International Inc., Morristown, NJ (US)

(*) Notice: Subject to any disclaimer, the term of this patent is extended or adjusted under 35 U.S.C. 154(b) by 1931 days.

(21) Appl. No.: 11/728,359

(22) Filed: Mar. 23, 2007

(65) Prior Publication Data

US 2008/0229831 A1   Sep. 25, 2008

(51) Int. Cl.
*B05D 5/12* (2006.01)
*G01N 29/02* (2006.01)
*B81C 1/00* (2006.01)
*G01N 29/24* (2006.01)
*G01N 7/00* (2006.01)

(52) U.S. Cl.
CPC ....... *G01N 29/022* (2013.01); *B81B 2201/0214* (2013.01); *B81C 1/00206* (2013.01); *G01N 29/2462* (2013.01); *G01N 2291/021* (2013.01); *G01N 2291/0423* (2013.01)

(58) Field of Classification Search
USPC .................................................. 427/100
See application file for complete search history.

(56) References Cited

U.S. PATENT DOCUMENTS

| | | | | |
|---|---|---|---|---|
| 4,699,966 A | * | 10/1987 | Harris et al. | 528/12 |
| 5,723,307 A | * | 3/1998 | Tsai et al. | 435/24 |
| 5,814,525 A | | 9/1998 | Renschler et al. | G01N 33/551 |
| 6,942,966 B1 | | 9/2005 | Cook | 435/6 |
| 6,951,690 B2 | | 10/2005 | Katz et al. | 428/447 |
| 2002/0115566 A1 | | 8/2002 | Sessler et al. | 504/218 |

(Continued)

FOREIGN PATENT DOCUMENTS

| | | | | |
|---|---|---|---|---|
| EP | 0598341 A1 | 5/1994 | | G01N 21/41 |
| EP | 0598341 B1 | 5/1994 | | G01N 21/41 |

(Continued)

OTHER PUBLICATIONS

Lieberzeit et al. 2005, Covalently anchored supramolecular monolayers on quartz surfaces for use in SAW sensors.*

(Continued)

*Primary Examiner* — Austin Murata
(74) *Attorney, Agent, or Firm* — Kermit D. Lopez; Luis M. Ortiz; Kevin Soules

(57) ABSTRACT

The design and deposition of a sensing layer for room temperature SAW/BAW chemical sensors utilizing macrocyclic compounds in accordance with supra-molecular chemistry principles. The gas to be sensed is attached to the organic sensing film thus changing its visco-elastic properties and creating a mass increase of the film deposited on the surface of SAW/BAW devices. A direct printing method can be used as an additive, mask-less procedure to deposit metallic interdigital transducers and electrodes required for SAW/BAW devices, along with the deposition of a guiding layer and the organic films only on the location required by the sensing SAW/BAW principle of the sensor. Different thermal treatment solutions can be used for the consolidation of the gelly organic films deposited by the direct printing methods.

6 Claims, 19 Drawing Sheets

(56) References Cited

U.S. PATENT DOCUMENTS

| | | | | |
|---|---|---|---|---|
| 2003/0077515 | A1 | 4/2003 | Chen et al. | 429/231.8 |
| 2003/0077656 | A1 | 4/2003 | Bordunov et al. | 435/7.1 |
| 2003/0170908 | A1* | 9/2003 | Bright et al. | 436/173 |
| 2004/0241462 | A1* | 12/2004 | Lee et al. | 428/447 |
| 2006/0019408 | A1* | 1/2006 | Waggoner et al. | 436/518 |
| 2006/0264672 | A1* | 11/2006 | Andrews et al. | 564/152 |
| 2007/0074577 | A1* | 4/2007 | Cobianu et al. | 73/715 |
| 2008/0093226 | A1* | 4/2008 | Briman et al. | 205/775 |

FOREIGN PATENT DOCUMENTS

| | | | | |
|---|---|---|---|---|
| FR | 2815351 A1 | 4/2002 | | C08G 77/06 |
| WO | WO 2005/066637 A1 | 7/2005 | | G01N 33/569 |

OTHER PUBLICATIONS

Zhao, Synthesis and properties of a water-soluble sing-walled carbon nanotube-poly(m-aminobenzene sulfonic acid.*

Drafts, "Acoustic Wave Technology Sensors" Oct. 2000.*

O. Tamarin, S. Comeau, C. Dejous, D. Moynet, D. Rebiere, J. Bezian, J. Pistre; Real Time Device for Biosensing: Design of a Bacteriophage Model Using Love Acoustic Waves; www.sciencedirect.com Biosensors and Bioelectronics 18 (2003) 755-763.

A.J. Ricco, SAW Chemical Sensors; 1046A Interface 3 (1994) Winter, No. 4, Pennington, NJ, US PCT—Notification of Transmittal of The International Search Report and The Written Opinion of the International Searching Authority, or the Declaration, Date of Mailing: Nov. 12, 2008.

Physicochemical Characterization of Covalently Bonded Alkyl Monolayers on Silica Surfaces; Y. Duvalut, A. Gagnaire, F. Gardies, N. Jaffnezicrenault, C. Martelet, D. Morel, J. Serpinet, J.L. Duvault; Thin Solid Films; 185 (1990) 169-179.

Synthesis of Amino-Silane Modified Superparamagnetic Silica Supports and Their Use for Protein Immobilization; X. Liu, J. Xing, Y. Guan, G. Shan, H. Liu; Colloids and Surfaces A: Physicochem. Eng. Aspects 238 (2004) 127-131.

Adsorption of Dyes on a Silica Surface; A. Krysztafkiewicz, S. Binkowski, T. Jesionowski; Applied Surface Science 199 (2002) 31-39.

Adsorbed Monolayers Versus Langmuir-Blodgett Monolayers—Why and How? I: From Monolayer to Multilayer by Adsorption; L. Netzer, R. Iscovici, J. Sagiv; Thin Solid Films 99 (1983) 235-241.

Sensor Materials for Solvent Vapor Detection—Donor—Acceptor and Host—Guest Interactions; F. L. Dickert, A. Haunschild; Advanced Materials 1993 5 No. 12.

Raman Spectroscopy of Covalently Bonded Alkylsilane Layers on Thin Silica Films Immobilized on Silver Substrates; W.R. Thompson, J.E. Pemberton; Department of Chemistry, University of Arizona; Analytical Chemistry, vol. 66, No. 20, Oct. 15, 1994.

Covalently Anchored Supramolecular Monolayers on Quartz Surfaces for Use in SAW Sensors; P.A. Lieberzeit, W. Greibl, H. Stathopulos, F.L. Dickert, G. Fischerauer, W.E. Buist; Elsevier, Articles in Press, Sensors and Actuators B (2005).

* cited by examiner

Where R = SO₃H

DEPOSITION OF SENSING LAYERS FOR SURFACE ACOUSTIC WAVE CHEMICAL SENSORS BASED ON SUPRA-MOLECULAR CHEMISTRY

TECHNICAL FIELD

Embodiments are generally related to SAW/BAW (Surface Acoustic Wave/Bulk acoustic wave) chemical sensors. Embodiments are additionally related to the design and deposition of organic sensing layers used in surface acoustic wave chemical sensors based on supra-molecular chemistry. Embodiments are also related to direct-printing methods for the realization of SAW-based chemical sensors.

BACKGROUND OF THE INVENTION

Gas detection at low temperature and low power consumption is a major concern for the field of chemical sensors primarily used in the context of wireless detection applications. In many gas sensing industrial applications, for example, metal oxide based chemo-resistors such as those based on $SnO_2$ can be used for the detection of reducing gases (e.g., $H_2$, CO, $CH_4$) and oxidizing gases (e.g., $NO_x$). The electrical resistance of $SnO_2$ gas sensors, for example, can increase in the presence of an oxidant gas, due to a charge transfer reaction between the $NO_x$ gas and metal oxide, which includes the removal of electrons from the metal oxide. On the other hand, in presence of a reducing gas, the electrical resistance of the same $SnO_2$ based sensor decreases due to a charge transfer reaction that supplies the chemo-resistor with electrons.

Depending on the type of gas, such sensors typically require high operating temperatures up to 450° C., which can cause the sensor to become a high-consumer of electric power typically in a consumption range of 30-200 mW. In MEMS (Micro-electro-mechanical System) gas sensor applications, the thermal isolation of a suspended membrane supporting a heated sensing layer is very high, but the power consumption can hardly be limited below 20 mW, for example, for producing a temperature of 400° C. Such levels of power consumption are considered high for some applications, even very high for wireless gas sensing applications.

Another important gas chemical sensor is a "pellistor", where a gas is detected due to an exothermic catalytic reaction with a heated surface, which further increases the temperature of the catalytic surface. This temperature increase further increases the resistance of a metallic resistor used for heating the surface. For example, a simple pellistor can be prepared from $Al_2O_3$ containing Pd catalysts, which covers the Pt resistor used for heating the catalyst material. Due to their intrinsic principle, the pellistors again consume an increased amount of electrical power, which may not be accepted in many future applications, including the wireless gas sensors.

In one prior art, exemplary polymeric film materials used on a SAW/BAW chemical sensor include, but are not limited to, polyisobutylene, polyphenylenesulphone, polyacrilic acid, polystyrene, polystyrene sulfonated, ethyl cellulose, polyethyleneimine, polyanilines, polyvinylpyrollidone, Teflon, Mylar, Kaladex, polyethylene adipate, polyethylenemaleate, polycaprolactone, polyethyleneglicols, polyepichlorohydrine, phenyl-methyl polysiloxanes, perfluoro-2, 2 dimethyl 1,3 dioxole (PDD), polypyrrole, etc. The interactions between sensitive polymeric, film and target molecules (gas molecules) include: π-π stacking, electrostatic, hydrogen bonding, size/shape recognition, van der Waals, acid-base.

In the prior art it has been demonstrated that analytes can be detected with a SAW/BAW chemical sensor. Such analytes can include, for example, but are not limited to non-polar vapours (hexane, toluene, octane), polar vapours (acetone, methanol), chlorinated hydrocarbons such as tetrachloroethylene (PCE), trichloroethylene (TCE), vinyl chloride (VC), carbon dioxide, carbon monoxide, ozone, nitric oxide, hydrofluoric acid, hydrogen sulphide, sulphur dioxide-, and so forth.

The organic sensing films utilized in a gas sensing application must be chemically and mechanically stable and can be applied onto the respective device surfaces by methods compatible to industrial standard coating procedures. The organic sensing films are typically deposited by spin-coating (in the case of polymer materials), or by evaporation (e.g., organic vapor phase deposition or in the case of small organic molecules). Similarly, the organic film is deposited on the entire surface and subsequently removed from the region where it is not necessary.

Based on the foregoing it is believed that a need exists for the realization of the chemical sensors operating at low temperatures, or even at room temperature. Additionally, a need exists for the synthesis and deposition of organic thin films-based gas chemical sensors operating at room temperature based on supra-molecular chemistry. Finally, a need exists for new and low-cost techniques for SAW chemical sensor fabrication, without the need for lithographic processes, which are expensive and can waste a great amount of material, which should be removed by etching from the areas where it is not required. It is believed that these and other problems can be solved by the solutions discussed herein, which generally relates to a SAW chemical sensor, wherein all the layers (e.g., metallic layer, dielectric layer, and/or functionalized sensing layer) for the fabrication of the sensors are accomplished by an additive processing technique, such as direct printing.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved SAW/BAW chemical sensor.

It is another aspect of the present invention to provide for an improved technique for fabricating a SAW chemical sensor based entirely on the direct printing of all types of layers (e.g., metallic layers, dielectric layers, functionalized sensing organic films, etc) required for sensor fabrication.

It is a further aspect of the present invention to provide for an improved method for the design and deposition of organic sensing layers for surface acoustic wave chemical sensors based on supra-molecular chemistry.

The aforementioned aspects and other objectives and advantages can now be achieved as described herein. A method and system are disclosed for the design and deposition of a sensing layer to be used in room temperature SAW/BAW chemical sensors utilizing macrocyclic compounds in accordance with supra-molecular chemistry principles. In general, the gas to be sensed becomes attached to an organic thin film, changes its visco-elastic properties and creates a mass increase of the organic sensing film deposited on the surface of SAW/BAW device. A direct printing method can be used as an additive, mask-less procedure to deposit metallic interdigital transducers and electrodes required for SAW/

BAW devices, along with the deposition of a guiding layer and the organic films only on the location required by the sensing SAW/BAW principle of the sensor. Different thermal treatment solutions can be utilized for the consolidation of the gelly organic films deposited by direct printing. The use of a "direct printing method" is thus a novel development for configuring a SAW chemical sensor, wherein all the layers involved in the fabrication are obtained by non-lithographic processes. Thus, there is not a need for masking and removal of later layers or components from different areas. For metallic layers directly printed on the piezoelectric substrate, a silver paste can be considered, as an example.

The supra-molecular chemistry principles such as, for example, host-guest chemistry, self assembly and static and/or dynamic molecular recognition can be utilized for the synthesis of macro-cyclic compound-based organic sensing films which includes four different chemical routes depending on the type of chemical bond of the organic layer to the piezoelectric substrate. The chemical routes for SAW/BAW sensing layers can be parent macrocyclic compounds covalently bonded to the substrate, polymeric calixarenes and crown ethers noncovalently bonded to the substrate, the attachment of supra-molecular receptors to polymeric support and PANI (polyanilines) doped with macrocyclic compounds based (bulky) counterions.

The structures of these macrocyclic ligands are defined by intramolecular cavities with various shapes and sizes, which are provided with appropriate binding sites and possess unique properties. Molecular and ionic species can be enclosed in these cavities through non-covalent interactions such as van der Waals forces, metal coordination, hydrogen bonding, pi-pi interactions, hydrophobic forces, electrostatic forces, etc. Different types of macrocyclic compounds that can be employed are: crown ethers, calixarenes, cyclodextrines, criptands, coronands, fullerenes, carbon nanotubes, carcerands, and so forth.

The SAW/BAW device utilized to implement the disclosed embodiment can detect gases and/or vapors of the following types: non-polar vapors (e.g., hexane, toluene, octane); polar vapors (e.g., acetone, methanol); aromatic and halogenated hydrocarbons such tetrachloroethylene-PCE, trichlororthylene-TCE, vinyl chloride-VC, carbon dioxide; carbon monoxide; ozone; nitric oxide; h hydrofluoric acid; hydrogen sulphide; sulphur dioxide, and so forth.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
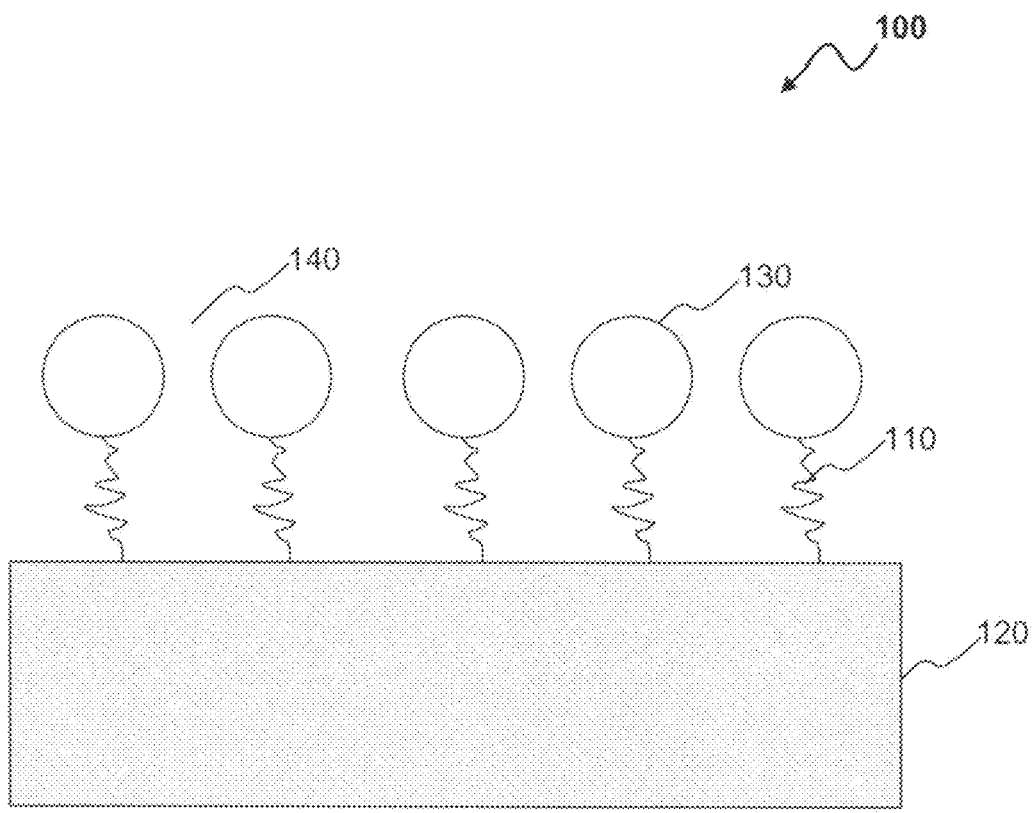
FIG. 1 illustrates a schematic diagram depicting organic sensing films with macrocyclic compound-based polymers covalently bonded to a piezoelectric quartz substrate, in accordance with a preferred embodiment.

Referring to FIG. 1 a schematic diagram illustrating organic sensing films with macrocyclic compounds covalently bonded to a piezoelectric substrate 100 is illustrated, in accordance with a preferred embodiment. As depicted in FIG. 1, an organic sensing film 140 with functionalized macrocyclic compound 130 can be covalently bonded to a piezoelectric substrate 120. The thin coating of solid state organic sensing film 140 for SAW/BAW sensing applications can be a functionalized macrocyclic compound 130 that forms a covalent bond 110 with the piezoelectric substrate 120, which is preferably provided in the form of a quartz substrate.

The functionalized macrocyclic compound 130 may be, for example, $\alpha,\beta,\gamma$ modified cyclodextrines (e.g., sulfonated cyclodextrines, amino cyclodextrines), calix[n]arenes and crown ethers, carcerands, coronands and criptands with appropriate pendant groups, each of them being able to be covalently bonded directly at the substrate 120. The strong bonding 110 can be possible due to the hydroxyl groups present onto the surface of the substrate 120. The reaction between piezoelectric substrate 120 and the macrocyclic compound 130 yields a monolayer which presents advantages such as: fast response, long-term stability, compact and robust design. Thus, due to the strength of the covalent bond 110, the delamination of the resulted sensing layer is improbable.

Figure 2A:
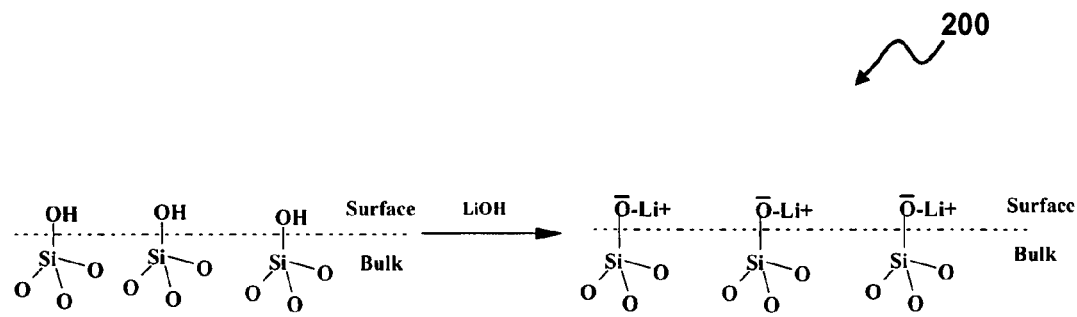
FIG. 2A illustrates a scheme demonstrating the reaction of hydroxyl groups on the surface of a piezoelectric substrate and lithium hydroxide for obtaining oxygen anions, in accordance with a preferred embodiment.
Figure 2B:
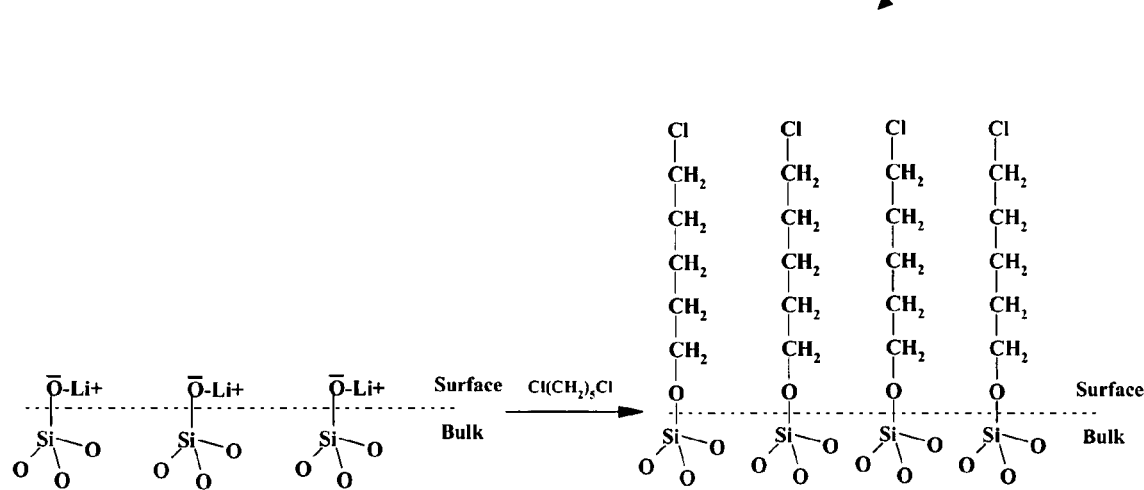
FIG. 2B illustrates a scheme demonstrating the reaction between oxygen anions and α,ω dihaloalkane with the formation of anchored halocompounds, in accordance with a preferred embodiment.
Figure 2C:
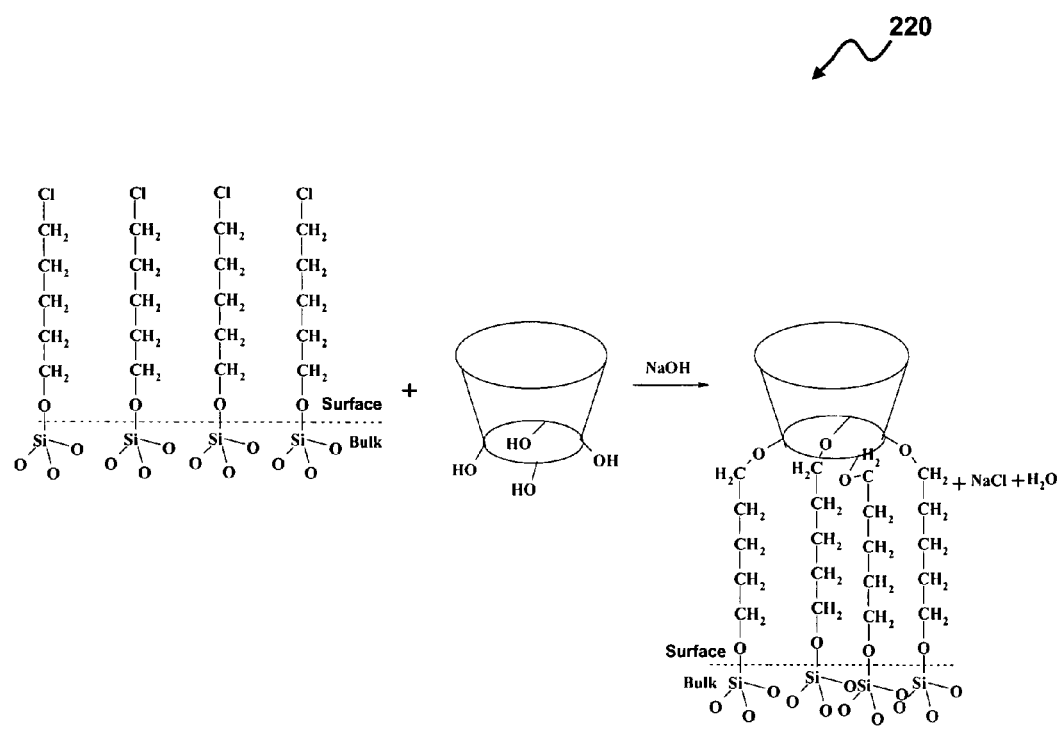
FIG. 2C illustrates a scheme demonstrating the reaction of halo-compound with calixarenes for anchoring calixarenes to the piezoelectric substrate, in accordance with a preferred embodiment.

The sequence of chemical reactions necessary for the preparation of an organic sensing film 140 of calix[4]arene, which is covalently bonded to the quartz substrate 120 is shown at FIGS. 2A-2C. The organic contaminants from the piezoelectric substrate 120 can be removed by cleaning in trichloro-ethylene followed by acetone and then alcohol. At the end of the process a DI deionizated-water cleaning and drying is carried out.

Referring to FIG. 2A a scheme 200 showing reaction of hydroxyl groups on the surface of the piezoelectric substrate and lithium hydroxide for obtaining oxygen anions is illustrated, which can be implemented in accordance with a preferred embodiment. The surface of the quartz substrate 120 is chemically treated with 0.2 M solution of lithium hydroxide for five minutes, and at the end of this reaction a large number of anions like O— can be obtained on the quartz substrate 120. These anions can be used as appropriate nucleophiles for further displacements.

Referring to FIG. 2B a scheme 210 showing reaction between oxygen anions and $\alpha,\omega$-dihaloalkane with formation of anchored halocompounds is illustrated, which can be implemented in accordance with a preferred embodiment. The "activated quartz" substrate 120 having O—Li+ ionic groups on the treated surface reacts with $\alpha,\omega$-dihaloalkane such as 1,5-dichloropentane, 1,6-dichlorohexane and 1,7 dichloroheptane based on Wiliamson-type synthesis. The product of this reaction is a polyether which contains reactive atoms of chlorine, as shown in FIG. 2B.

Referring to FIG. 2C, a scheme 220 is illustrated that demonstrates the reaction of halo-compound with calixarenes for anchoring calixarenes to quartz substrate, in accordance with a preferred embodiment. The previously obtained halo compound obtained reacts with a solution of calix[n]arene compound (e.g., parent p-tert butyl calix[4,6,8] arenes and derivatives of these compounds with different pendant groups), which was initially neutralized in a basic medium of NaOH, followed by a Williamson-type synthesis, as depicted in FIG. 2A and FIG. 2B. At the end of the reaction the calix[4]arene organic monolayer is covalently bonded on the quartz substrate 120. Finally, the quartz substrate 120 can be washed with dry ethanol-chloroform (1:1 solution) followed by rinsing in DI water and drying. The above procedure can be utilized to detect aromatic and halogenated hydrocarbons when the sensing monolayer is calixarene. If the functionalized sensing monolayer is cyclodextrine, then vapors of alcohols or freons can be detected. If the cavity of the host as depicted in FIG. 2C possesses a large dimension, then the host cavities can adopt different shapes, thereby allowing for dynamic molecular recognition of different guest molecules. Therefore, the bigger the host cavity, the larger the amount of guest molecules can be detected. On the other hand by designing the host cavities with a smaller size, the sensing selectivity can be increased.

Figure 12:
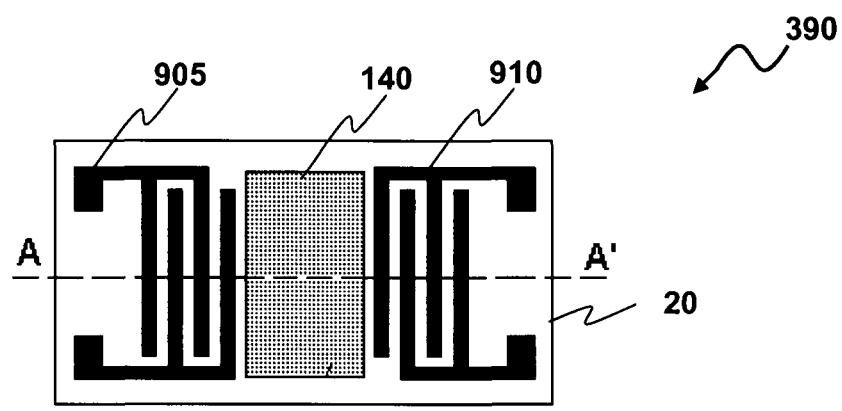
FIG. 12 illustrates a front view of a SAW gas sensor, which can be implemented in accordance with a preferred embodiment, of all direct printing processes.
Figure 13:
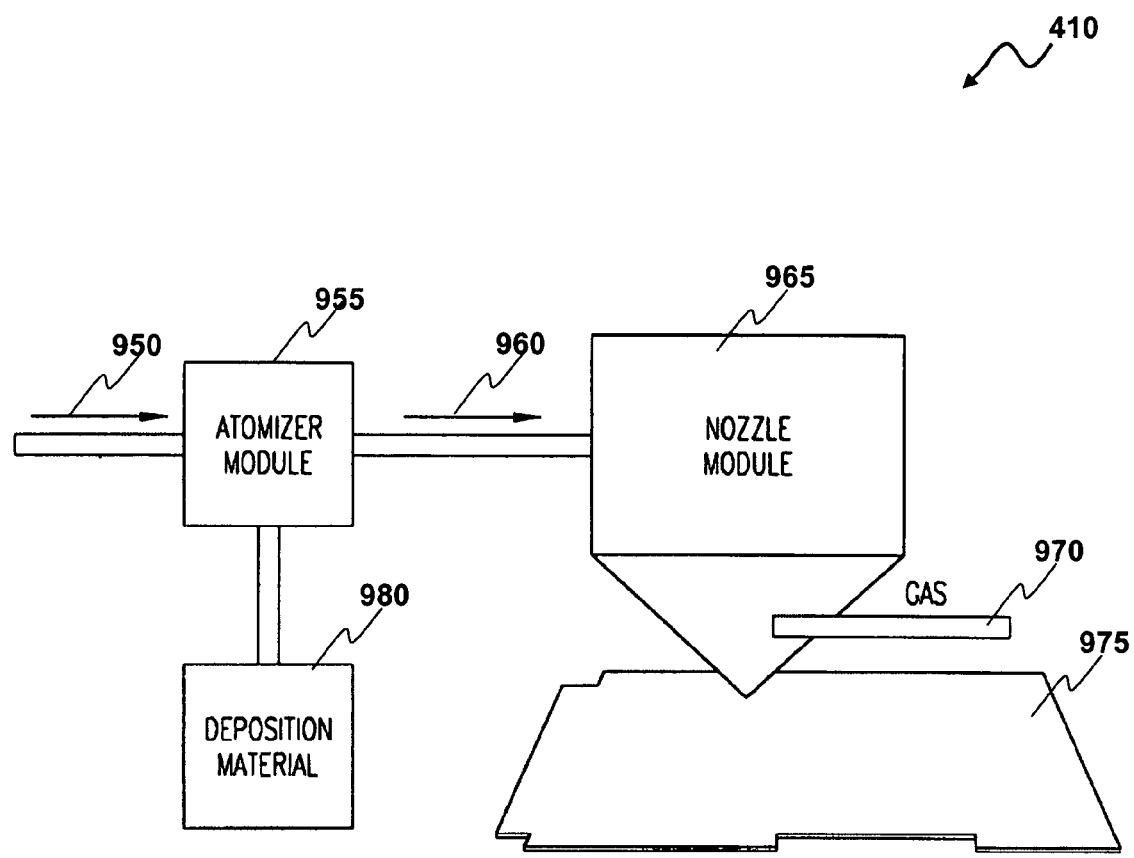
FIG. 13 illustrates a schematic diagram of a direct-printing apparatus for the deposition of metallic layers, dielectric wave guide layer and/or organic film in a liquid state, in accordance with a preferred embodiment.

The selective deposition of the above compounds on the quartz substrate 120 can be carried out by utilizing a direct printing method as depicted in FIG. 13. The direct printing method allows depositing the organic sensing film 140 in a mask less and additive manner only in the region between interdigital transducers (IDT) 905 and 910 as shown in FIG. 12 of the SAW devices, and thus avoiding loading the region of IDT 905 and 910 with organic sensing layer 140. Note that a preferred method for use in configuring metallic layers and dielectric wave guide components is the direct printing method(s) described herein.

Figure 3:
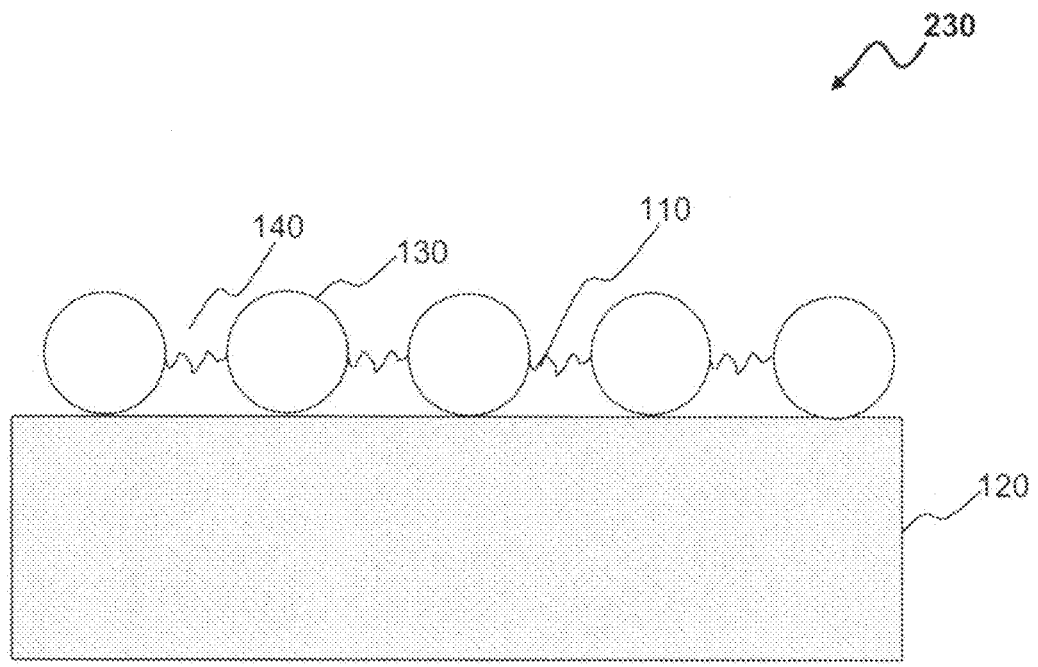
FIG. 3 illustrates a schematic diagram depicting organic sensing films with macrocyclic compound-based polymers non-covalently bonded to a piezoelectric substrate, in accordance with a preferred embodiment.

Referring to FIG. 3 a schematic diagram showing organic sensing films with macrocyclic compound-based polymers non-covalently bonded to piezoelectric substrate 230 is illustrated in accordance with a preferred embodiment. As shown in FIG. 3, the organic sensing layer 140 can be deposited on the piezoelectric (quartz) substrate 120, when the substrate 120 bonding forces are of non-covalent type. The adherence forces of macrocyclic compound-based polymers 130 to the substrate 120 can have different origins like: hydrogen bonding or Van der waals forces. A solution of surfactants (e.g., anionic surfactants, cationic surfactants, nonionic surfactants, and zwiter-ionic) can be used for increasing the adherence to the substrate 120.

The homogeneous liquid phase of the polymeric calixarenes can be prepared by the polymerization or co-polymerization of a suitable monomer (macrocyclic receptor). Preparation of thin solid organic sensing film 140 of polymeric calixarenes, which are non-covalently bonded to the piezoelectric substrate 120, can be performed in three steps.

Figure 3A:
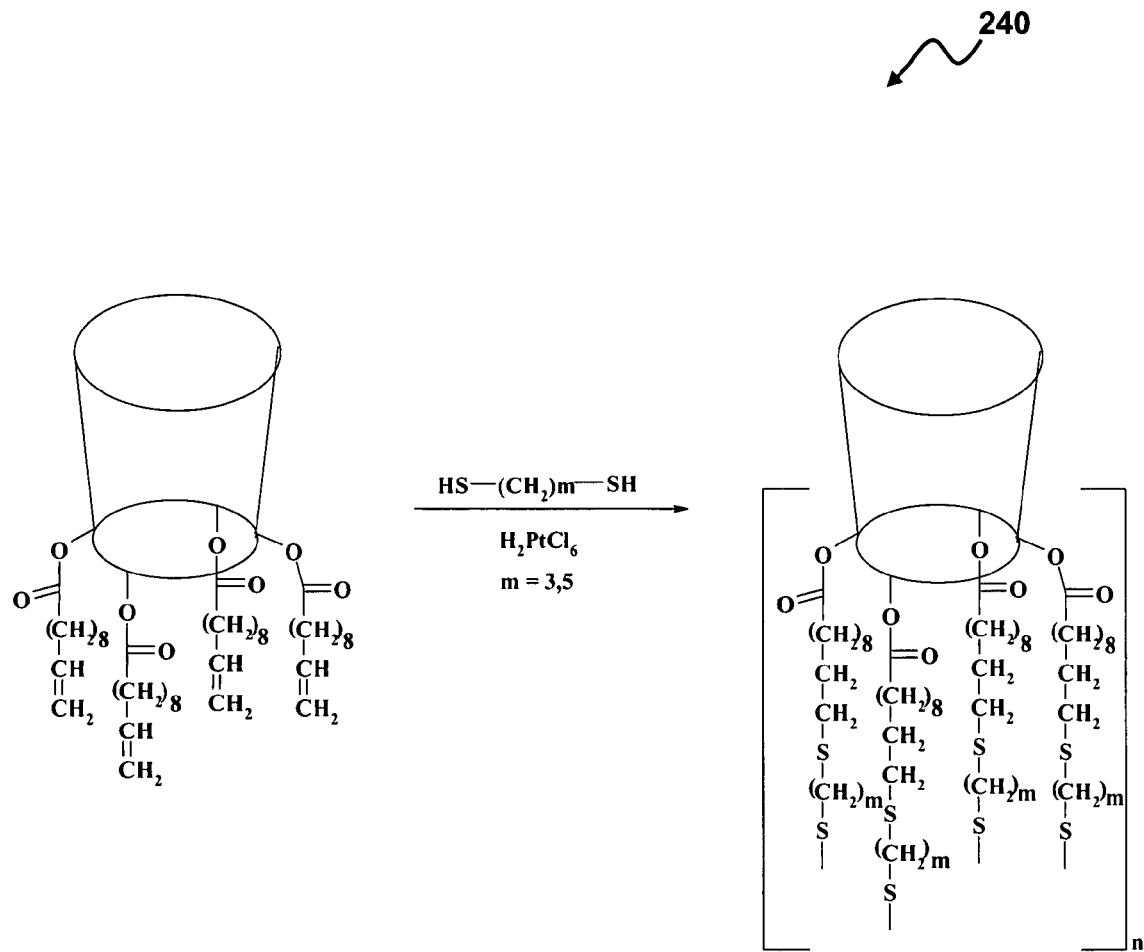
FIG. 3A illustrates a scheme demonstrating the polymerization reaction of 5,11,17,23-tetra-p-tertbutyl, 25,26,27,28-tetra-10-undecenoxy calix[4]arene with α,ω-dithiols, in the presence of $H_2PtCl_6$ as catalyst in accordance with a preferred embodiment.

Referring to FIG. 3A a scheme 240 showing polymerization reaction of 5,11,17,23-tetra-p-tertbutyl,25,26,27,28, tetra10-undecenoxy calix[4]arene with α,ω-dithiols is illustrated, which can be implemented in accordance with a preferred embodiment. In the first step, Einhorn procedure can be followed, for the reaction between p-tert-butylcalix[4]arene and 10-undecenoyl chloride and the compound 5,11, 17,23,tetra-p-tertbutyl,25,26,27,28,tetra10-undecenoxy calix[4]arene can be obtained, which is an ester represented as in the left member of FIG. 3A In the second step the polymerization reaction of the above obtained ester can be carried out with α,ω dithiols in the presence of hexachloroplatinic acid as catalyst and a calixarene based polymer can be obtained.

In the third step, dimethyl sulphoxide solution of calixarene-based polymer obtained as above can be converted into a solid film by film deposition methods like spin coating, dip coating, spray coating or drop casting followed by thermal consolidation of the "gelly" layer obtained immediately after deposition on the quartz substrate 120. The direct printing method as shown in FIG. 13 can be used for the selective deposition of the above liquid compounds on the quartz substrate 120, only on the surface region where it is required by sensing principle of SAW/BAW devices, followed by layer consolidation by different method like thermal treatment or laser treatment or UV lamp treatment. During this last step removal of solvent from the matrix and film densification can take place. The target molecules to be detected by these polymeric calixarenes are, for example: aromatic organic compounds depending on the size and design of macrocyclic ligands.

Figure 4:
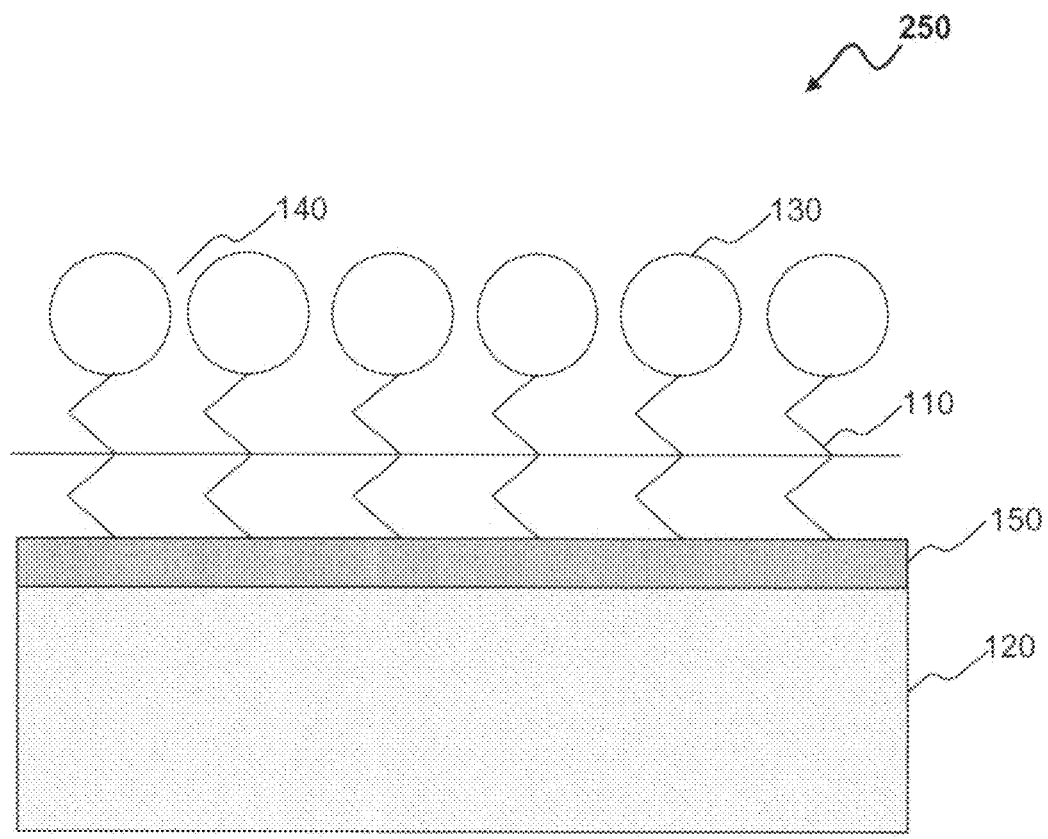
FIG. 4 illustrates a schematic diagram depicting an organic macrocyclic compound covalently bonded to a polymeric layer deposited on the piezoelectric substrate, in accordance with a preferred embodiment.

Referring to FIG. 4 a schematic diagram of an organic macrocyclic compound covalently bonded to a polymeric layer deposited on piezoelectric substrate 250 is illustrated, in accordance with a preferred embodiment. The sensing organic film 140 based on a supra-molecular receptor forms a covalent bond 110 to a polymeric layer 150 deposited on the piezoelectric substrate 120. The route of chemical synthesis is composed of the following steps.

Figure 5A:
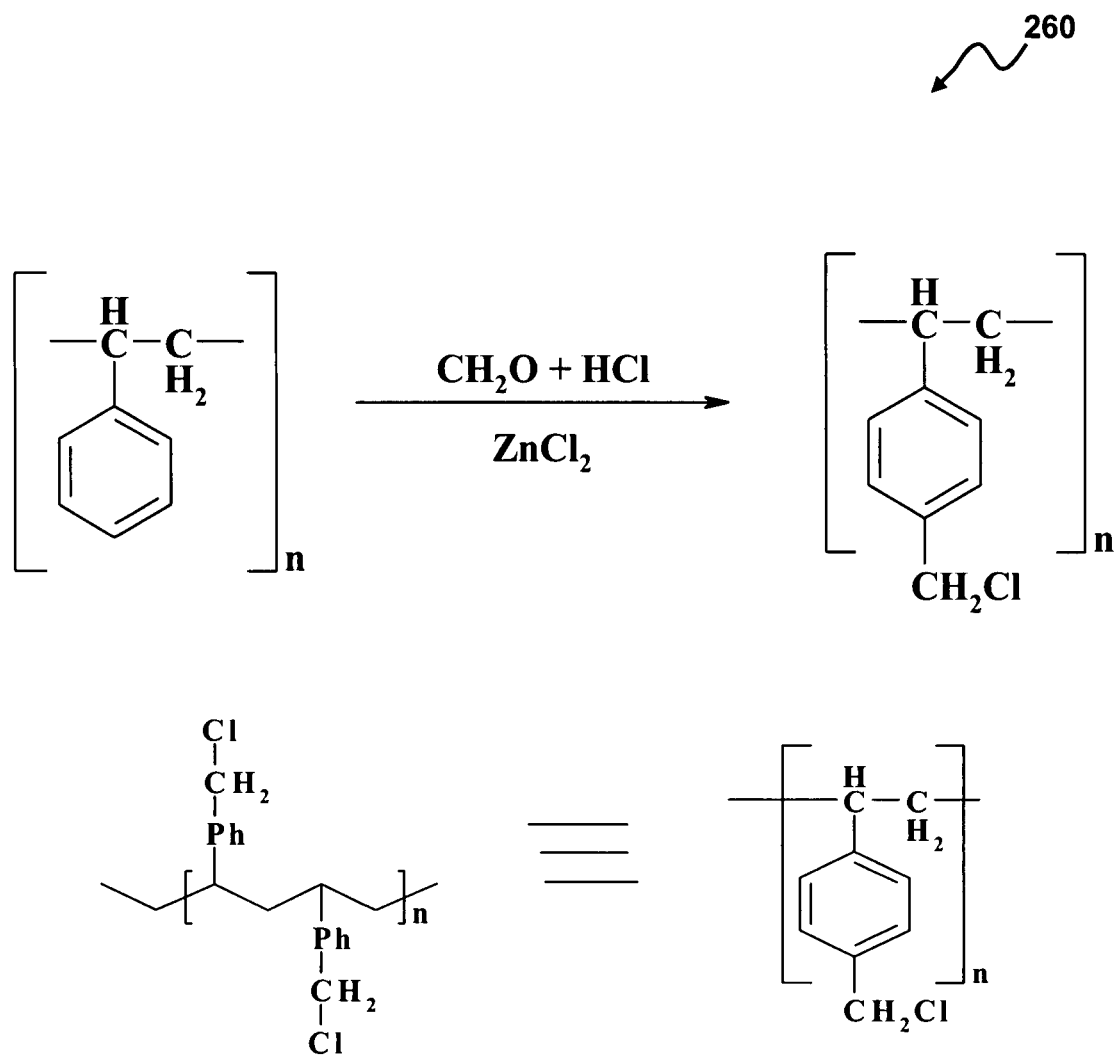
FIG. 5A illustrates a scheme showing reaction of polystyrene with formaldehyde and hydrochloric acid in the presence of zinc chloride as catalyst with formation of chloromethylated polystyrene, which can be implemented in accordance with a preferred embodiment.

Referring to FIG. 5A a scheme 260 showing a reaction of polystyrene with formaldehyde and hydrochloric acid with formation of chloromethylated polystyrene is illustrated, which can be implemented in accordance with a preferred embodiment. In the first step, polystyrene reacts with formaldehyde and hydrochloric acid in presence of zinc chloride as Lewis acid catalyst with formation of chloromethylated polystyrene, according to chloromethylation Blank procedure, as shown in FIG. 5A.

Figure 5B:
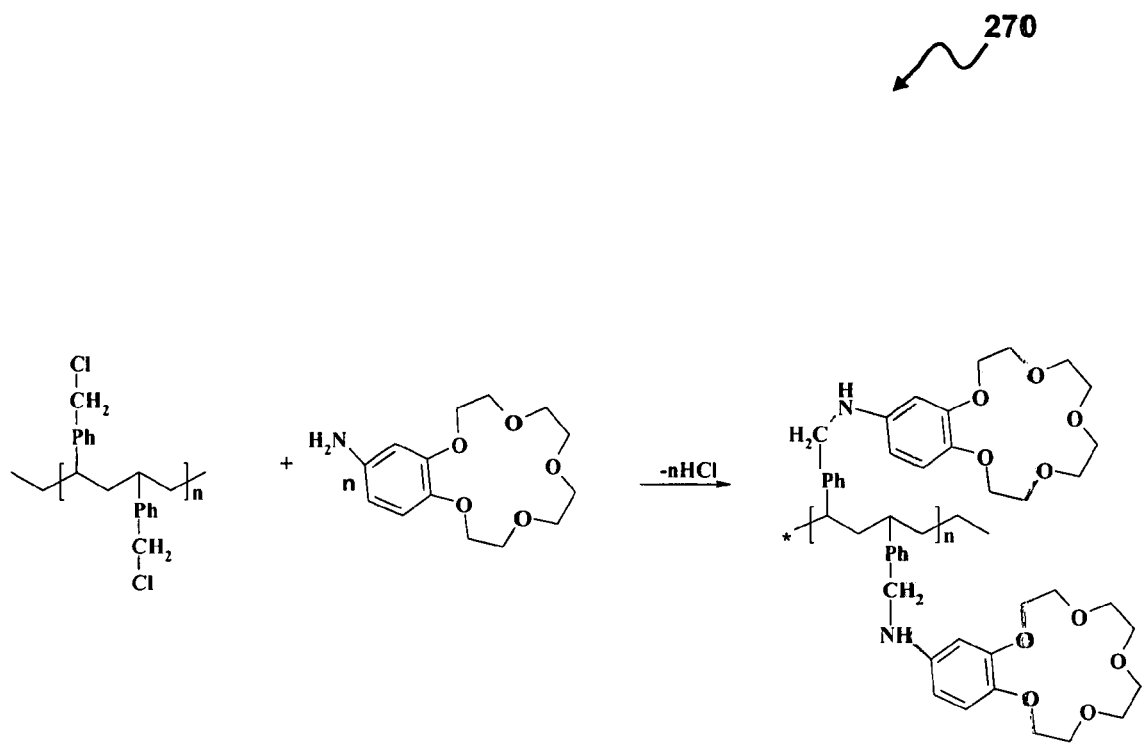
FIG. 5B illustrates a scheme showing reaction of chloromethylated polystyrene with 4-aminobenzo-15-crown-5 with formation 4-aminobenzo-15-crown-5 based polymer according to Hoffman-type alkylation, which can be implemented in accordance with a preferred embodiment.

Referring to FIG. 5B a scheme 270 showing a reaction of chloromethylated polystyrene with 4-aminobenzo-15-crown-5 with formation 4-aminobenzo-15-crown-5 based polymer according to Hoffman-type alkylation is illustrated, which can be implemented in accordance with a preferred embodiment. In the second step, chloromethylated polystyrene reacts with 4-aminobenzo-15-crown-5 in a Hoffman-type alkylation with formation of 4-aminobenzo-15-crown-5 based polymer. The solution of this type of polymer in dimethyl sulphoxide is direct printed onto the surface of a device, as shown in FIG. 13. An alternative route for the synthesis of these organic sensing films 140 based on supra-molecular receptors that form a covalent bond 110 to the polymeric layer 150 can be as follows.

Figure 6A:
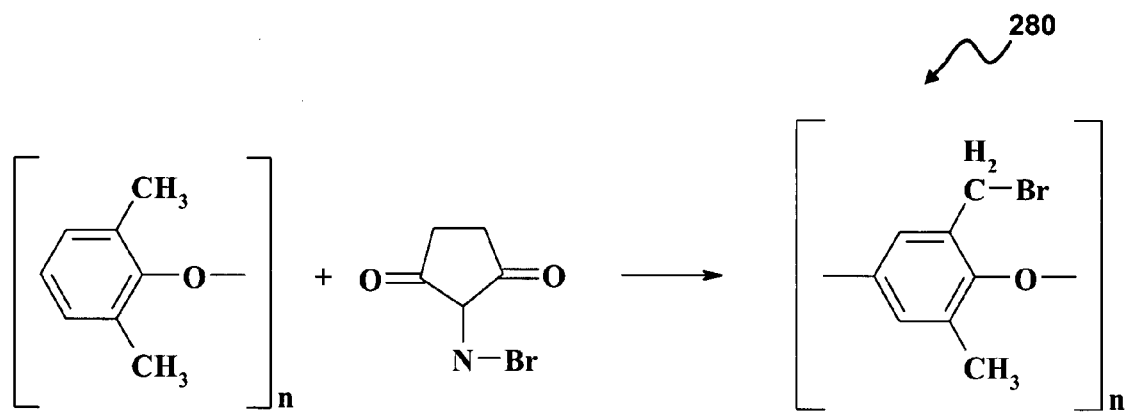
FIG. 6A illustrates a scheme showing a reaction between 2,6-dimethyl-1,4-phenylene oxide (PPO) and N-bromo-succinimide (NBS) with formation of brominated PPO, according to a Wohl-Ziegler procedure, which can be implemented in accordance with a preferred embodiment.

Referring to FIG. 6A a scheme 280 showing a reaction between 2,6-dimethyl-1,4-phenylene oxide (PPO) and N-bromo-succinimide (NBS) with formation of brominated PPO, according to a Wohl-Ziegler procedure is illustrated, which can be implemented in accordance with a preferred embodiment. In the first step, the 2,6-dimethyl-1,4-phenylene oxide (PPO) reacts with N-bromo-succinimide (NBS) according to a Wohl-Ziegler procedure, in order to obtain brominated PPO.

Figure 6B:
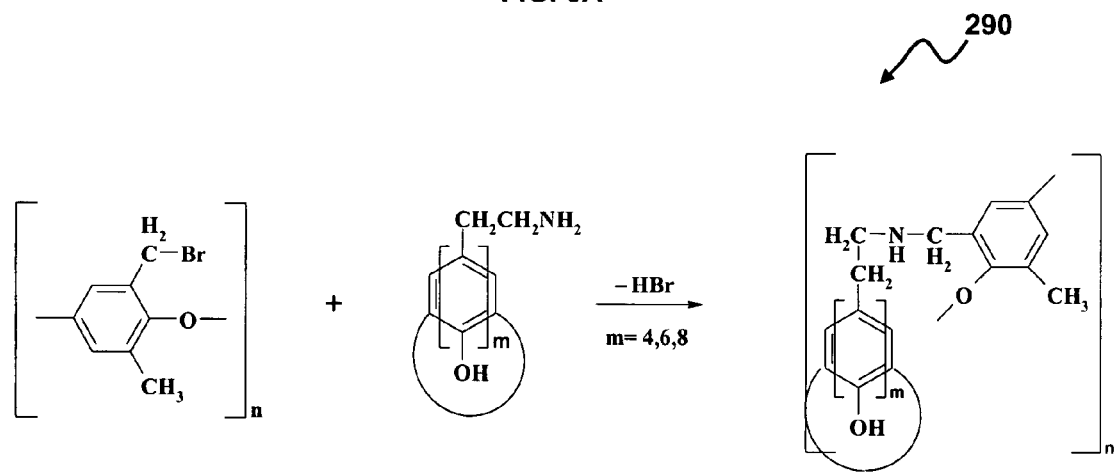
FIG. 6B illustrates a scheme showing a reaction between brominated PPO containing benzylic bromine atoms with amino calix[n]arene with formation of the amino calixarene-based PPO, which can be implemented in accordance with a preferred embodiment.

Referring to FIG. 6B a scheme 290 showing a reaction between the brominated PPO containing benzylic bromine atoms with amino calix[n]arene for obtaining amino calixarene-based PPO is illustrated, which can be implemented in accordance with a preferred embodiment. In the second step, the brominated PPO containing benzylic bromine atoms reacts with amino calix[n]arene in order to obtain the amino calixarene-based PPO. The resulting solution of amino calixarene-based PPO can be used for deposition of the sensing layer 140 by direct printing deposition method as shown in FIG. 13.

Figure 6C:
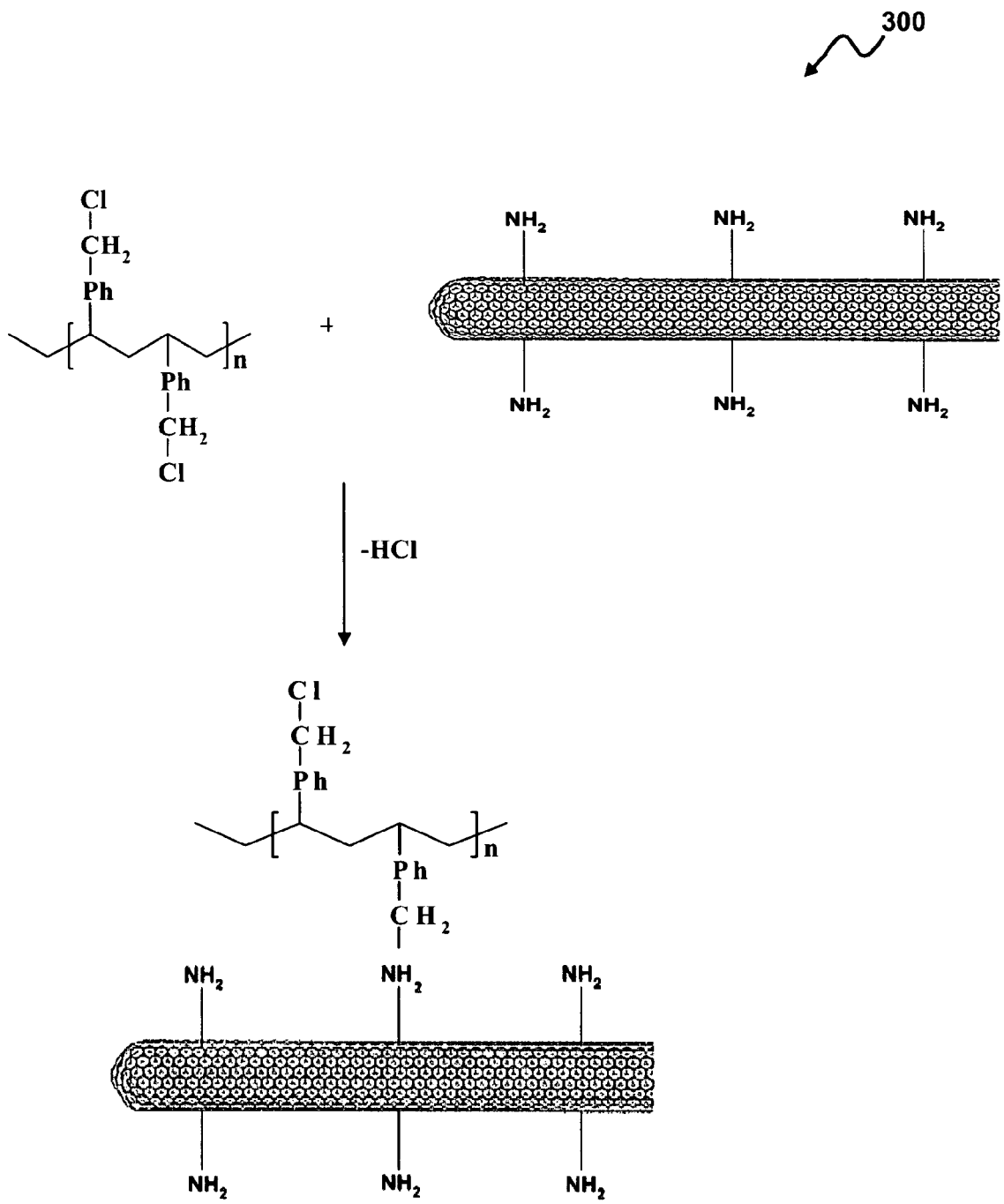
FIG. 6C illustrates a scheme showing a reaction between chloromethylated polystyrene and aminocarbon nanotubes (CNT) for obtaining amino CNT based PPO, which can be implemented in accordance with a preferred embodiment.

Referring to FIG. 6C a scheme 300 demonstrates the reaction between chloromethylated polystyrene and amino carbon nano tubes (CNT) for obtaining amino CNT based chloromethylated polystyrene in accordance with a preferred embodiment. Chloromethylated polystyrene dissolved in dimethyl formamide (DMF) reacts with aminocarbon nanotubes (dissolved in the same DMF) in an ultrasonic bath for about six hours in order to obtain aminocarbon nanotubes-based chloromethylated polystyrene. Another similar procedure for preparation of the organic sensing film 140 based on supra-molecular receptors that forms a covalent bond 110 to polymeric support 150 is described below.

Figure 7:
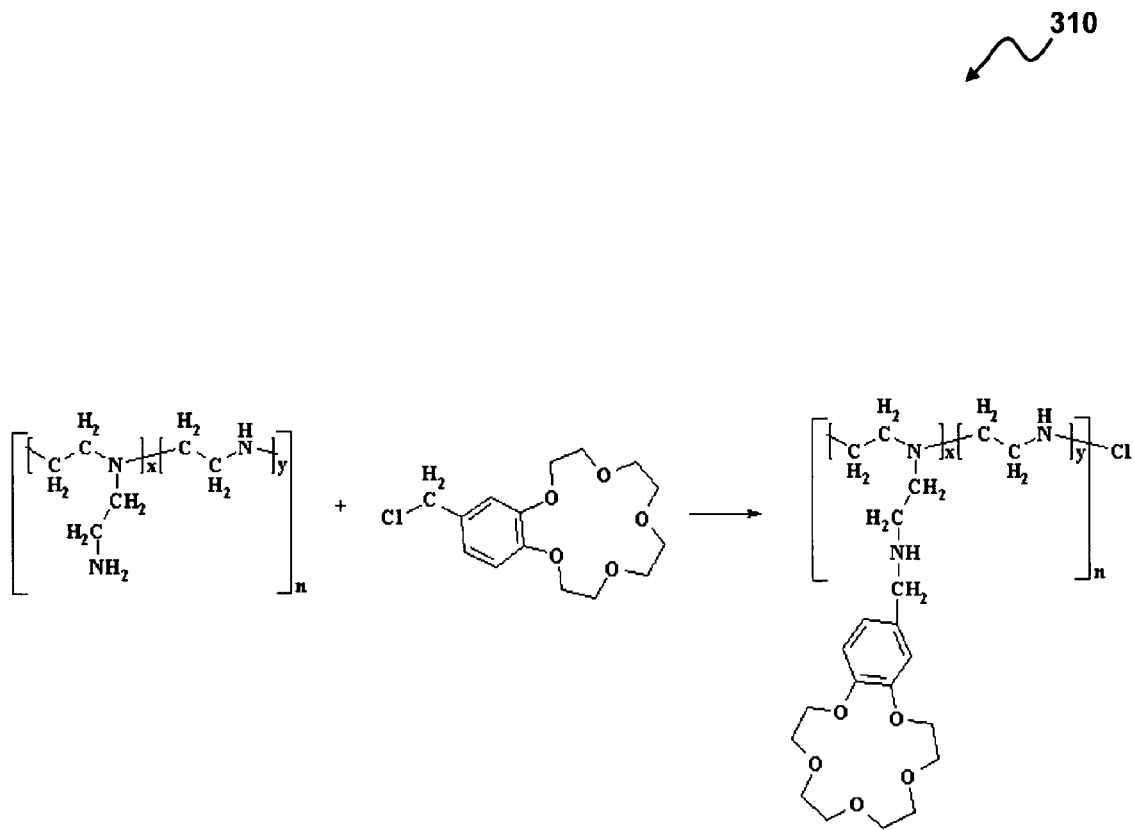
FIG. 7 illustrates a scheme showing a reaction between polyethyleneimine (PEI) and 4'chloromethylbenzo-15-crown-5 with formation of PEI functionalized with benzo-15-crown-5 syntons based on Hofmann-type alkylation, which can be implemented in accordance with a preferred embodiment.

Referring to FIG. 7 a scheme 310 showing reaction between polyethyleneimine (PEI) and 4'chloromethylbenzo-15-crown-5 with formation of PEI functionalized with benzo-15-crown-5 syntons based on Hofmann-type alkylation is illustrated, which can be implemented in accordance with a preferred embodiment. The polyethyleneimine (PEI) reacts with 4'chloromethylbenzo-15-crown-5 in a Hofmann-type alkylation with formation of PEI functionalized with benzo-15-crown 5 syntons. This liquid form can be dissolved in DMF and can be deposited on the quartz substrate 120 by direct printing method as shown in FIG. 13.

Solutions of these types of polymers dissolved in DMF can be deposited on the quartz substrate 120 by the direct printing method as shown in FIG. 13. The bonds between organic sensing film 140 and piezoelectric substrate 120 can be, for example, hydrogen bonds, van der Waals interactions etc. These bonds are responsible for the stability of the organic sensing film 140 onto the piezoelectric substrate 120. Solution of surfactants (e.g., anionic surfactants, cationic surfactants, non-ionic surfactants, and zwitterionic) can be used for increasing the adherence. Note that a preferred method for use in configuring metallic layers and dielectric wave guide components is the direct printing method(s) described herein. The target molecules to be detected are aromatic hydrocarbons, acetone, hydrogen sulphide, ammonia, carbon dioxide, etc.

Figure 8:
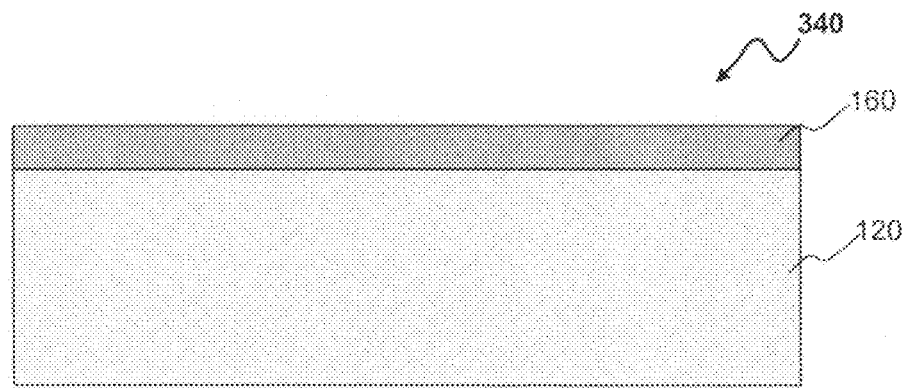
FIG. 8 illustrates a schematic diagram illustrating PANI polymers doped with macrocyclic compounds containing bulky organic counterions deposited on the piezoelectric substrate, in accordance with a preferred embodiment.

Referring to FIG. 8 a schematic diagram showing PANI polymers doped with macrocyclic compounds containing bulky organic counterions deposited on the surface of piezoelectric substrate 340 is illustrated, which can be implemented in accordance with a preferred embodiment. The PANI polymers 160 doped with macrocyclic compound containing bulky organic counter ions are deposited on the surface of piezoelectric substrate 120, where no covalent bonding is established between the sensing film 140 and the substrate 120.

Figure 9:
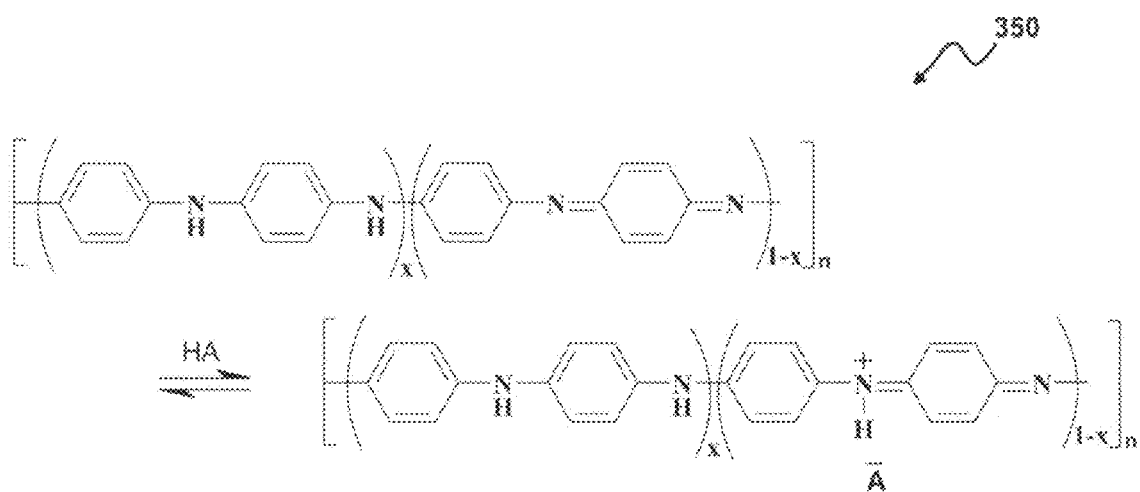
FIG. 9 illustrates a scheme depicting a sensing film configured from a substituted PANI (polyaniline) doped with protonic acid HA in an acid-base equilibrium, in accordance with a preferred embodiment.

Referring to FIG. 9 a scheme 350 showing sensing film made of substituted PANI (polyaniline) doped with protonic acid HA in an acid-base equilibrium is illustrated, which can be implemented in accordance with a preferred embodiment. The organic sensing film 140 in this case is substituted polyanilines doped with protonic acid HA in an acid base equilibrium.

Figure 10:
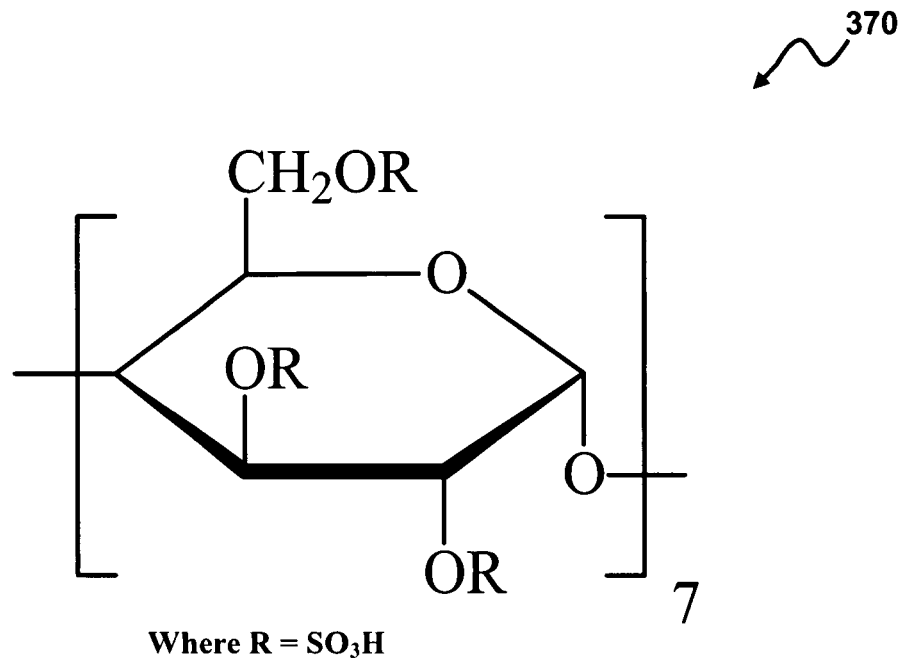
FIG. 10 illustrates a structure of sulfonato-cyclodextrines (alfa, beta, gamma), as an example of HA dopant containing large organic counterions, which can be implemented in accordance with a preferred embodiment.

Referring to FIG. 10 a structure 370 of sulfonato-cyclodextrines (alfa, beta, gamma), as an example of an HA dopant containing large organic counterions is illustrated, which can be implemented in accordance with a preferred embodiment. The dopant HA possesses large organic counterions such as: carboxylic acid of calix[n]arenes, sulfonato-cyclodextrines (alfa, beta, gamma), as shown in FIG. 10 and sulfonated crown ethers such as: 3'-sulfobenzo-12-crown-4(SB12C4), 3'-sulfobenzo-15-crown-5 (SB15C5), 3'-sulfobenzo-18-crown-6 (SB18C6), di(3'-sulfo)dibenzo-18-crown-6 (DSDB18C6), di(3'-sulfo)-dibenzo-21-crown-67 (DSDB21C7), di(3'-sulfo)-dibenzo-24-crown-8 (DSDB24C8).

Figure 11:
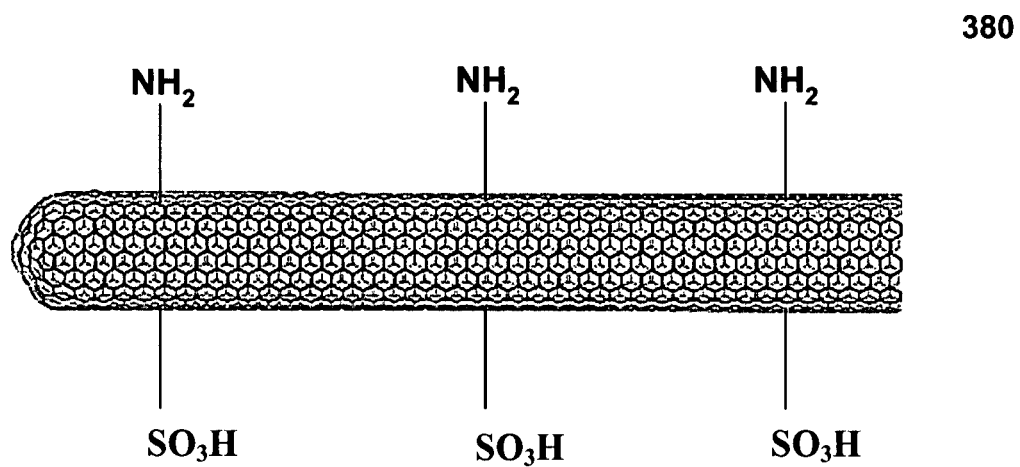
FIG. 11 illustrates a structure of sulfonato aminocarbon nanotubes, as another dopant with large organic counterions, which can be implemented in accordance with a preferred embodiment.

Referring to FIG. 11 a structure 380 of sulfonato aminocarbon nanotubes, as another dopant with large organic counterions is illustrated, which can be implemented in accordance with a preferred embodiment. The polymer 160 is deposited on the piezoelectric substrate 120 through direct printing method as shown in FIG. 13. The target molecules detected are ammonia, carbon dioxide and water. The selectivity of this coating is ensured both of polyaniline as sensitive polymer for ammonia, water, carbon dioxide, and dopant due to the host-guest relationship.

Figure 12A:
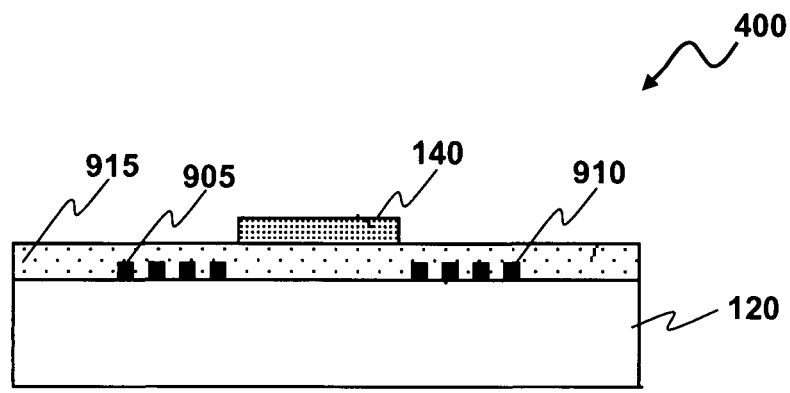
FIG. 12A illustrates a sectional view A-A of the SAW gas sensor depicted in FIG. 12, which can be implemented in accordance with a preferred embodiment.

Referring to FIG. 12 a front view of a SAW gas sensor element 390 is illustrated, which can be implemented in accordance with a preferred embodiment. A SAW gas sensor based on Love waves is shown in FIG. 12. The gas sensor 390 generally includes a substrate 120, which is preferably provided in the form of a quartz substrate. A metal layer can be deposited on the substrate 120, which can be patterned to obtain the interdigital (IDT) structure 905 and 910. A guiding layer 915 as shown in FIG. 12A can be deposited above the metal interdigital (IDT) structure 905 and 910 specific to all SAW devices for the conversion of the electrical energy to mechanical energy and the opposite by the piezoelectric effect.

The guiding layer 915 should be further patterned and a selective removal of some regions of the guiding layer 915 may be required for allowing access to the electrical pads of the sensor. The preferred fabrication method with respect to the metallic layers (not shown) and/or a dielectric wave guide layer/component 915 is a direct printed process as shown in FIG. 13. A preferred (but not the only method) method involves depositing the metal layer (not shown) and the wave guide layer 915 directly in the desired region, without the need for further patterning and etching. Such a direct printing technique can be utilized with respect to all layers required for fabrication of a SAW chemical gas sensor. The use of direct printing in this manner will reduce costs, while providing rapid-prototyping advantages.

The gas sensor element functions are based on the changes of mass load and the visco-elastic properties of the sensing layer 140 located in the region in between the two IDT's 905 and 910. Not that the sensing layer 140 can function as, for example, a metal layer, a wave guide layer 915, an organic sensing film 140 and/or a combination thereof. The selective deposition of the metal, wave guide layer 915 and/or organic sensing film 140 on the quartz substrate 120 can be accomplished utilizing a direct printing method as shown in FIG. 13. Love waves are produced if the shear velocity of the wave in the guiding layer 915 is lower than that in the substrate 120. In the Love wave-based SAW device 390, the wave generated in the piezoelectric substrate 120 by the input inter digitized transducer (IDT) 905 is trapped in the guiding layer 915 and travels to the second IDT (Output IDT) 910 where the energy of the mechanical wave is transformed into the energy of an electrical signal. Note that a Love wave is a shear type wave and has a significant magnitude for certain cuts and orientation of piezoelectric crystals.

The metallic materials for metal interdigital (IDT) structure 905 and 910 can be preferably aluminum or gold. The thickness of these metal electrodes for IDT fabrication is around 0.1 micrometers in order to provide optimum reflectivity and mechanical charging. After metal patterning, the guiding layer 915 and the organic sensing film 140 can be deposited. The guiding layer 915 must have high viscosity, so that the acoustic wave cannot be attenuated. Silicon oxides or zinc oxides can be used as guiding layers. The guiding layer thickness depends on the SAW operation frequency and it is in the range from 2 micrometers to 7 micrometers for frequencies ranging from 80 MHz to 400 MHz. The organic sensing film 140 is deposited by direct printing method as shown in FIG. 13 in the region between the input interdigital (IDT) transducer 905 and the output IDT 910.

The consolidation of the organic sensing layer 140 can be accomplished by thermal annealing taking into consideration the maximum temperature at which the organic sensing layer 140 can preserve chemical stability and sensing properties. The direct printing method allows depositing the organic sensing layer 140 in a mask less and additive manner only in the region between interdigital transducers (IDT) 905 and 910 of the SAW devices, and thus avoiding loading the region of IDT with sensing layers 140. In the case of the preferred direct printing method for a metal layer, a material such as silver, gold, and/or copper can be utilized, while a wave guide layer 915 can be configured utilizing a commercially-available spin-on-glass material (e.g., silicon dioxides) in accordance with the requirements for the wave guide thickness and reflective index value for the specific application and its ultimate target of maximum signal at the sensor output.

Referring to FIG. 12A a sectional view A-A of a SAW gas sensor 400 depicted in FIG. 12 is illustrated, which can be implemented in accordance with a preferred embodiment. Note that in FIGS. 1-10, identical or similar parts or elements are generally indicated by identical reference numerals.

Referring to FIG. 13 a schematic diagram of direct printing equipment 410 for the deposition of a metallic layer, a dielectric wave guide layer and/or an organic sensing film in the liquid state is illustrated, which can be implemented in accordance with a preferred embodiment. The direct printing equipment 990 generally includes an atomizer module 955 for atomizing liquid and particle suspensions which directs and focus the atomized material 960 through a nozzle module 965 into the substrate 120. The deposition material 980 is delivered to the atomizer module 955 utilizing a carrier gas 950. The carrier gas is most commonly compressed air or an inert gas, where one or both may contain modified solvent vapor content. The viscosity of the deposited fluid can be increased by partial evaporation of the solvent. This increased viscosity allows for greater control of the lateral spreading of the organic film 140 as it contacts the substrate 120. The combined streams exit through a nozzle module 965 which focuses the organic film 140 onto the substrate 28.

The liquid phase of the metal, wave guide layer 915 and the organic sensing film 140 is deposited exactly in the region where it is required and thus a material savings can be attained. There is no further need for subsequent lithographical process to remove the metal or guiding layer 915 from regions where it is not required, such as in the case of pad for the electrical connection of the SAW device with external electrical signals. The deposition of the organic sensing film 140 can be proposed as the last process in the fabrication technology, where the sensing layer 140 is directly printed after the sensor packaging, so that damaging the organic compounds due to the temperature budget of the packaging process can be avoided.

The deposition in the liquid phase of the metal and guiding layer 915 assures good film uniformity due to spreading of the liquid phase on the substrate 120. The gel transition is obtained at the transfer of the liquid on the substrate 120, while the solid state transition of the direct printed film is obtained by further thermal annealing, taking into consideration the thermal limitation imposed by the type of metal used, and thickness of the guiding layer 915. The thermal treatment for "firing" and further densification of the "gelly" layer could be a local laser treatment tuned in such a way so that to avoid layer cracking and overheating of the metal layer from below the guiding layer. When thicker layers are needed, the direct printed method can be repeated till the necessary thickness is obtained.

Figure 14:
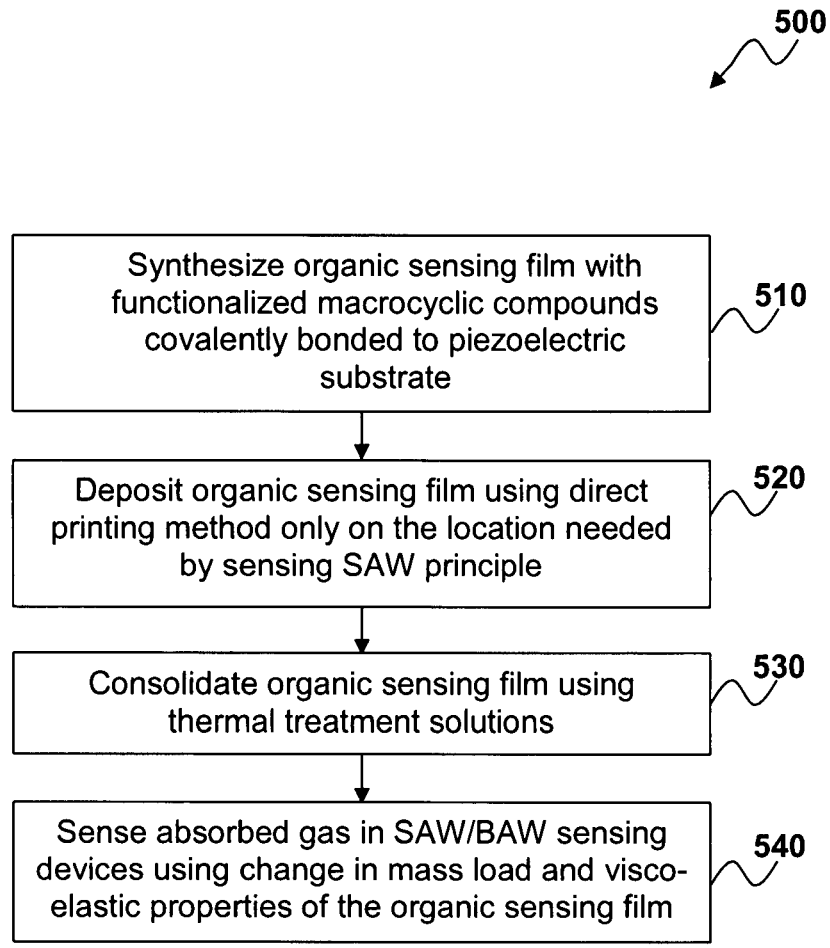
FIG. 14 illustrates a detailed flow chart of operations illustrating logical operational steps of a method for the design and deposition of organic sensing layers based on parent macrocyclic ligands, in accordance with a preferred embodiment.

Referring to FIG. 14 a detailed flow chart of operations illustrating logical operational steps of a method 500 for the design and deposition of organic sensing layers based on parent macrocyclic ligands is illustrated, in accordance with a preferred embodiment. Note that the metal layers for interdigital transducers 905 and 910 and electrodes as well as the dielectric guiding layer 915 utilized as a wave guide for some SAW chemical gas sensor applications can also be fabricated via a direct printing method, such as those described herein. The organic sensing film 140 with functionalized macrocyclic compounds 130 covalently bonded to the piezoelectric substrate 120 can be synthesized, as indicated at block 510. The organic sensing film 140 can be deposited utilizing the direct printing method 410 only on the location required by sensing SAW principle, as indicated at block 520. Thereafter, the organic sensing film 140 can be consolidated utilizing thermal treatment solutions, as depicted at block 530. The absorbed gas in SAW/BAW sensing devices can be sensed utilizing a change in the mass load and visco-elastic properties of the organic sensing film 140, as indicated at block 540.

Figure 15:
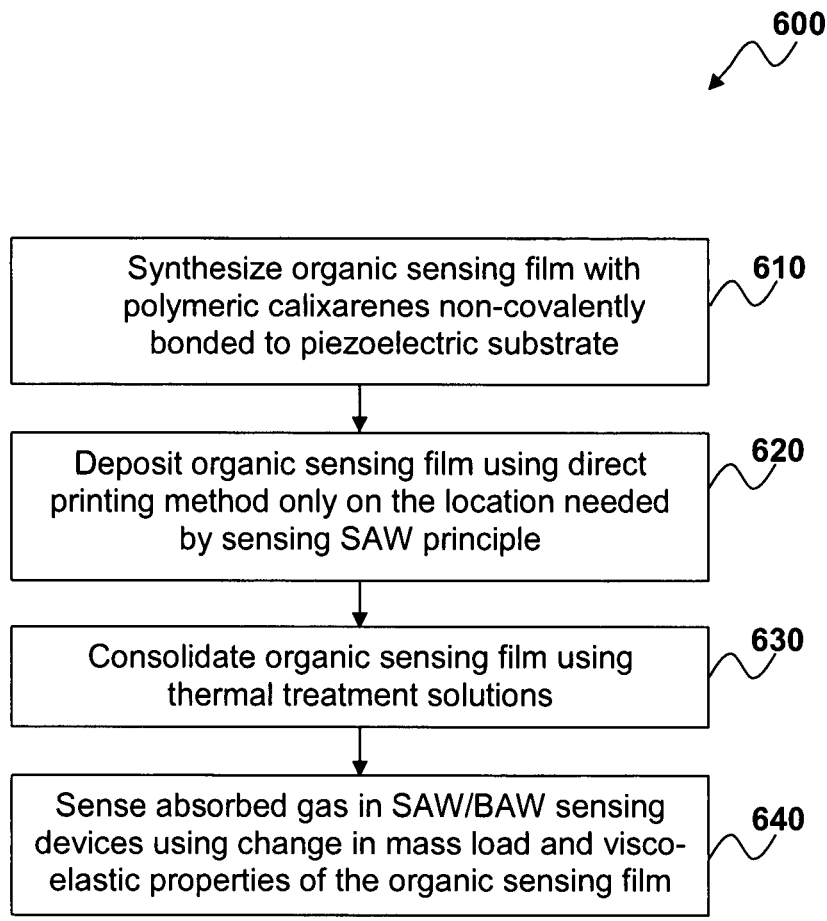
FIG. 15 illustrates a detailed flow chart of operations illustrating logical operational steps of a method for the design and deposition of organic sensing layers based on polymeric calixarenes and crown ethers, in accordance with a preferred embodiment.

Referring to FIG. 15 a detailed flow chart of operations illustrating logical operational steps of a method 600 for the design and deposition of organic sensing layers based on polymeric calixarenes and crown ethers is illustrated, in accordance with a preferred embodiment. Note that the preferred method for metallic layers and a dielectric wave guide layer 915 is also the direct printing method(s) described herein. The organic sensing film 140 with polymeric calixarenes non-covalently bonded to piezoelectric substrate 120 can be synthesized, as indicated at block 610. The organic sensing film 140 can be deposited utilizing the direct printing method 410 only on the location required by the sensing SAW principle, as indicated at block 620. Thereafter, the organic sensing film 140 can be consolidated utilizing thermal treatment solutions, as depicted at block 630. The absorbed gas in SAW/BAW sensing devices can be sensed utilizing change in mass load and visco-elastic properties of the organic sensing film 140, as indicated at block 640.

Figure 16:
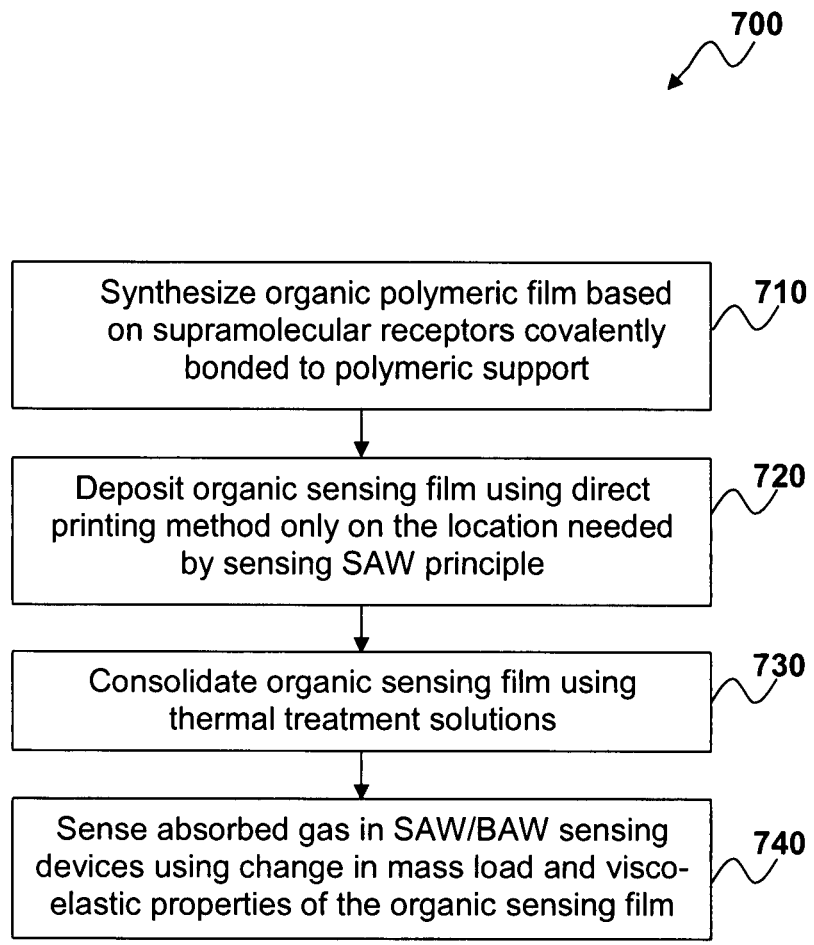
FIG. 16 illustrates a detailed flow chart of operations illustrating logical operational steps of a method for the design and deposition of organic sensing layers based on the attachment of supra-molecular receptors to polymeric support, in accordance with a preferred embodiment.

Referring to FIG. 16 a detailed flow chart of operations illustrating logical operational steps of a method 700 for the design and deposition of organic sensing layers based on the attachment of supra-molecular receptors to polymeric support is illustrated, in accordance with a preferred embodiment. Note that the preferred method for metallic layers and a dielectric wave guide layer 915 is also the direct printing method(s) described herein. The organic polymeric film based on supra-molecular receptors covalently bonded to polymeric support 150 can be synthesized, as indicated at block 710. The organic sensing film 140 can be deposited utilizing a direct printing method 410 only on the location required by sensing SAW principle, as indicated at block 720. Thereafter, the organic sensing film 140 can be consolidated utilizing thermal treatment solutions, as depicted at block 730. The absorbed gas in SAW/BAW sensing devices can be sensed utilizing a change in the mass load and visco-elastic properties of the organic sensing film 140, as indicated at block 740.

Figure 17:
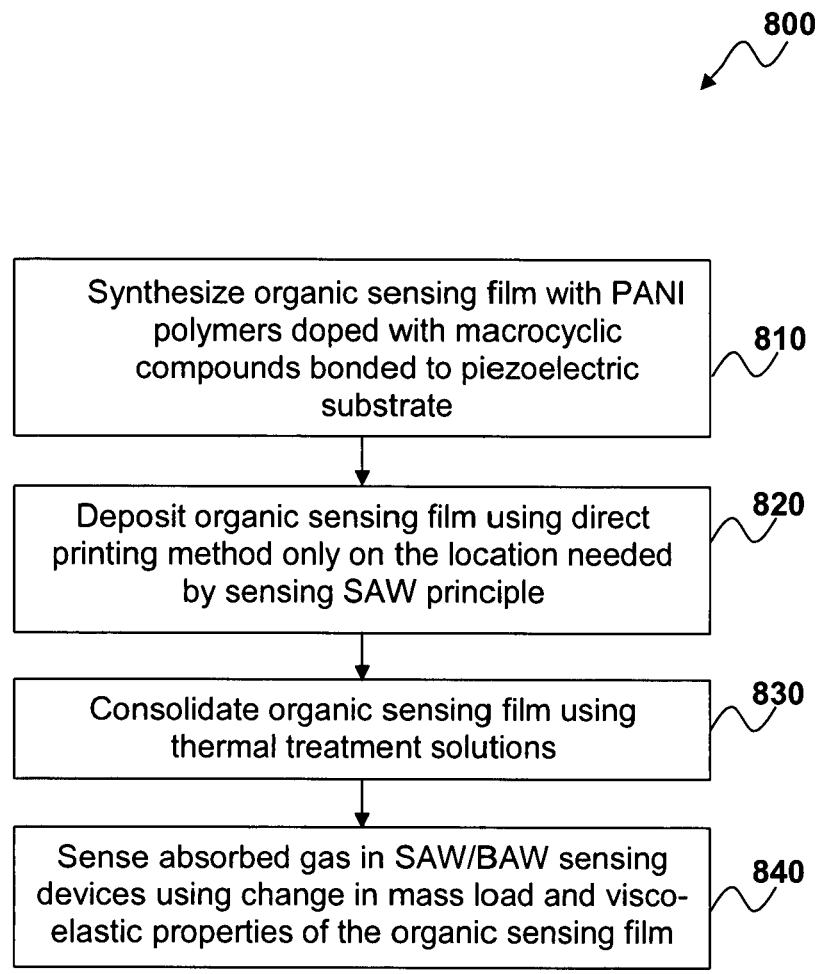
FIG. 17 illustrates a detailed flow chart of operations illustrating logical operational steps of a method for the design and deposition of organic sensing layers based on polyanilines doped with macrocyclic compounds, in accordance with a preferred embodiment.

Referring to FIG. 17, a detailed flow chart of operations illustrating logical operational steps of a method 800 for the design and deposition of organic sensing layers based on polyanilines doped with macrocyclic compounds is illustrated, in accordance with a preferred Note, however, that a preferred method for use in depositing metallic layers and dielectric wave guide layers 915 and/or components is also the direct printing method(s) discussed herein. The organic sensing film 140 with PANI polymers 160 doped with macrocyclic compounds bonded to piezoelectric substrate 120 can be synthesized, as indicated at block 810. The organic sensing film 140 can be deposited utilizing the direct printing method 410 only on the location required by sensing SAW principle, as indicated at block 820. Thereafter, the organic sensing film 140 can be consolidated utilizing thermal treatment solutions, as depicted at block 830. The absorbed gas in SAW/BAW sensing devices can be sensed utilizing a change in mass load and visco-elastic properties of the organic sensing film 140, as indicated at block 840.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for the design and deposition of organic sensing layers for surface acoustic wave chemical sensors, comprising:

designing and synthesizing an organic sensing film based on a plurality of chemical routes, wherein one chemical route is selected from said plurality of chemical routes using a dynamic molecular recognition principle;

synthesizing said organic sensing film based on at least one polymeric calixarenes non-covalently bonded to said piezoelectric substrate;

preparing a homogeneous liquid phase of said at least one polymeric calixarenes by means of a polymerization or copolymerization of a monomer with at least one $\alpha,\omega$-dithiol wherein said monomer comprises 25,26,27,28-tetra10-undecenoxy calix[4]arene obtained by reacting p-tertbutylcalix[4]arene with a 10-undecenoyl chloride;

depositing said designed and synthesized organic sensing film over a dielectric wave guiding layer on a plurality of electrodes pre-formed on a piezoelectric substrate forming a gelly organic sensing film; and consolidating said gelly organic sensing film utilizing at least one thermal treatment solution comprising a local laser treatment applied to avoid cracking said gelly organic sensing film, to form said organic sensing film, thereby forming a gas sensor for the detection of a plurality of gases utilizing a change in mass load and visco-elastic properties of said organic sensing film.

2. The method of claim 1 wherein depositing said organic sensing film over said dielectric wave guiding layer on a plurality of electrodes pre-formed on a piezoelectric substrate further comprises:

depositing, utilizing a maskless direct printing operation, said organic sensing film and said guiding layer on said plurality of electrodes pre-formed on said piezoelectric substrate.

3. The method of claim 1 wherein depositing said organic sensing film over said dielectric wave guiding layer on a plurality of electrodes pre-formed on a piezoelectric substrate further comprises:

depositing, utilizing at least one classical deposition operation, said organic sensing film and said wave guiding layer on said plurality of electrodes pre-formed on said piezoelectric substrate.

4. The method of claim 1 wherein said at least one $\alpha,\omega$-dithiol is 1,3-dithiolpropane.

5. The method of claim 1 wherein a plurality of target molecules to be detected by said at least one polymeric calixarene comprises an aromatic hydrocarbon and a volatile organic compound.

6. A method for the design and deposition of organic sensing layers for surface acoustic wave chemical sensors, comprising:

designing and synthesizing an organic sensing film based on a plurality of chemical routes;

synthesizing said organic sensing film based on at least one polymeric calixarenes non-covalently bonded to said piezoelectric substrate;

preparing a homogeneous liquid phase of said at least one polymeric calixarenes by means of a polymerization or copolymerization of a monomer with at least one $\alpha,\omega$-dithiol wherein said monomer comprises 25,26,27,28-tetra10-undecenoxy calix[4]arene obtained by reacting p-tertbutylcalix[4]arene with a 10-undecenoyl chloride;

depositing, utilizing a maskless direct printing operation, said organic sensing film and a dielectric wave guiding layer on a plurality of electrodes pre-formed on said piezoelectric substrate;

consolidating said organic sensing film utilizing at least one thermal treatment solution, thereby forming a gas sensor for the detection of a plurality of gases utilizing a change in mass load and visco-elastic properties of said organic sensing film.

* * * * *